United States Patent
Kim et al.

(10) Patent No.: US 11,103,803 B2
(45) Date of Patent: Aug. 31, 2021

(54) DISTILLATION DEVICE AND DISTILLATION METHOD

(71) Applicant: LG CHEM, LTD., Seoul (KR)

(72) Inventors: Tae Woo Kim, Daejeon (KR); Sung Kyu Lee, Daejeon (KR); Joon Ho Shin, Daejeon (KR); Yeon Uk Choo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/619,391

(22) PCT Filed: Jun. 8, 2018

(86) PCT No.: PCT/KR2018/006502
§ 371 (c)(1),
(2) Date: Dec. 4, 2019

(87) PCT Pub. No.: WO2018/226056
PCT Pub. Date: Dec. 13, 2018

(65) Prior Publication Data
US 2020/0179820 A1    Jun. 11, 2020

(30) Foreign Application Priority Data

Jun. 8, 2017   (KR) .................... 10-2017-0071649

(51) Int. Cl.
*B01D 3/14* (2006.01)
*B01D 1/28* (2006.01)
(Continued)

(52) U.S. Cl.
CPC .......... *B01D 1/2856* (2013.01); *B01D 3/143* (2013.01); *B01D 5/0063* (2013.01); *C07C 7/005* (2013.01);
(Continued)

(58) Field of Classification Search
CPC .... B01D 1/2856; B01D 3/143; B01D 5/0063; C07C 7/005; C07C 7/04; C10G 53/02
See application file for complete search history.

(56) References Cited

U.S. PATENT DOCUMENTS 4,277,268 A * 7/1981 Spangler, Jr. ........ B01D 1/2856
203/24
4,718,986 A * 1/1988 Comiotto ................ C07C 7/005
203/26

(Continued)

FOREIGN PATENT DOCUMENTS

CN        105749573 A    7/2016
JP         33156732 A    6/1988
(Continued)

*Primary Examiner* — Jonathan Miller
(74) *Attorney, Agent, or Firm* — Dentons US LLP

(57) ABSTRACT

A distillation device including: a first distillation column having first top, bottom and upper outlets and first upper and lower inlets; a second distillation column equipped with a top condenser and a bottom reboiler, and having second top, bottom and upper outlets and second upper and lower inlets; a vapor recompressor; a heat exchanger; a first supply line supplying a feedstock to the first lower inlet; a first connection line transferring a first bottom flow to the second lower inlet via the heat exchanger; and a second connection line transferring a second top flow to the top condenser via the heat exchanger after passing through the vapor recompressor. The first bottom flow flowing through the first connection line and the second top flow flowing through the second connection line are heat-exchanged in the heat exchanger. A distillation method of a feedstock using the distillation device.

15 Claims, 3 Drawing Sheets

(51) Int. Cl.
  *B01D 5/00* (2006.01)
  *C07C 7/00* (2006.01)
  *C07C 7/04* (2006.01)
  *C10G 53/02* (2006.01)

(52) U.S. Cl.
  CPC ............... *C07C 7/04* (2013.01); *C10G 53/02* (2013.01); *C10G 2400/20* (2013.01); *C10G 2400/22* (2013.01)

(56) References Cited

U.S. PATENT DOCUMENTS

| | | | | |
|---|---|---|---|---|
| 5,252,187 | A * | 10/1993 | Ohtsu | B01D 1/26 159/24.2 |
| 5,294,304 | A * | 3/1994 | Kano | C07C 29/84 203/19 |
| 8,182,654 | B2 * | 5/2012 | Sechrist | B01D 3/14 203/26 |
| 9,550,133 | B2 * | 1/2017 | Favilli | B01D 3/14 |
| 9,770,674 | B2 * | 9/2017 | Lee | C07C 7/04 |
| 9,851,140 | B2 * | 12/2017 | Wakabayashi | F25J 1/0022 |
| 10,022,648 | B2 * | 7/2018 | Maedebach | B01D 3/007 |
| 10,486,080 | B2 * | 11/2019 | Choo | C07C 37/08 |
| 10,737,195 | B2 * | 8/2020 | Brown | B01D 3/146 |
| 2008/0302650 | A1 | 12/2008 | Bello | |
| 2010/0197987 | A1 * | 8/2010 | Almering | C07C 7/04 585/671 |
| 2015/0299075 | A1 * | 10/2015 | Lee | C07C 29/80 203/22 |
| 2016/0082363 | A1 * | 3/2016 | Lee | C07C 9/15 203/21 |
| 2017/0203230 | A1 * | 7/2017 | Raiser | B01D 3/007 |

FOREIGN PATENT DOCUMENTS

| | | |
|---|---|---|
| JP | 035432 A | 1/1991 |
| JP | 2000-273468 A | 10/2000 |
| JP | 3128809 B2 | 11/2000 |
| JP | 2012-45449 A | 3/2012 |
| JP | 5481808 B2 | 2/2014 |
| JP | 5756900 B2 | 6/2015 |
| JP | 2016525448 A | 8/2016 |
| JP | 2017064588 A | 4/2017 |
| KR | 10-2008-0089961 A | 10/2008 |
| KR | 10-2015-0016137 A | 2/2015 |
| KR | 10-2016-0051665 A | 5/2016 |
| KR | 10-2016-0052416 A | 5/2016 |
| WO | 2012-012153 A2 | 1/2012 |
| WO | 2015/033935 A1 | 3/2015 |
| WO | 2016068676 A1 | 5/2016 |
| WO | 2016182234 A1 | 11/2016 |

* cited by examiner

[Figure 1]
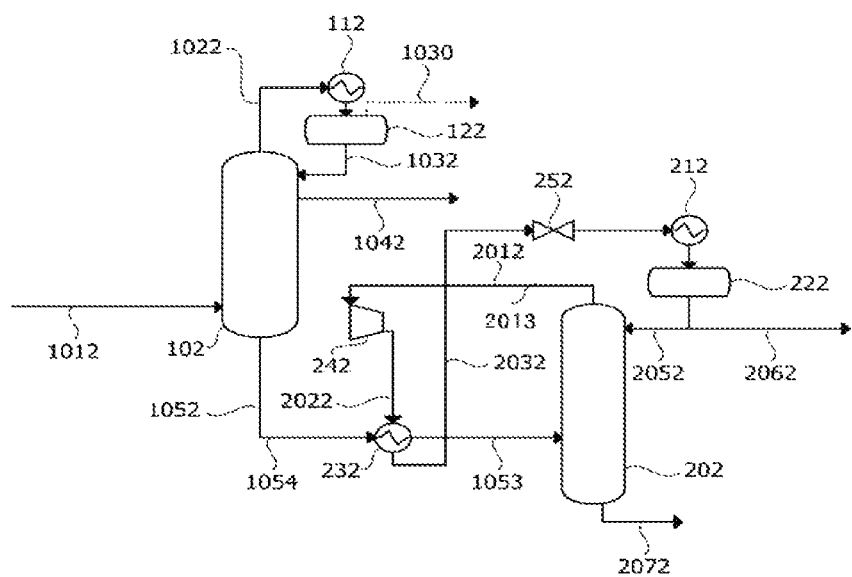

[Figure 2]
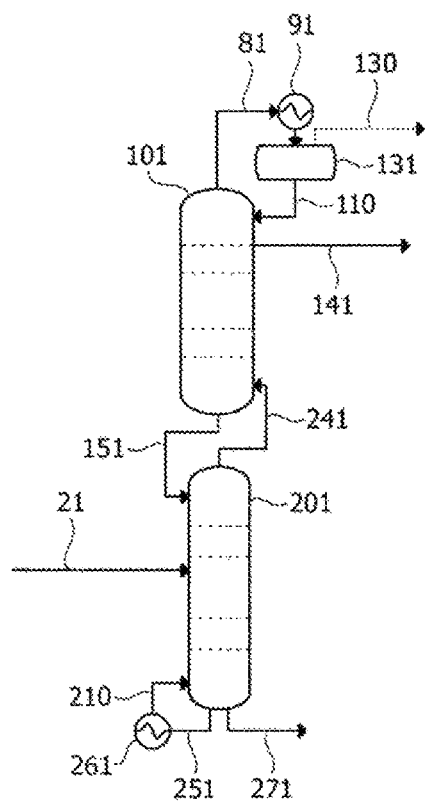

[Figure 3]
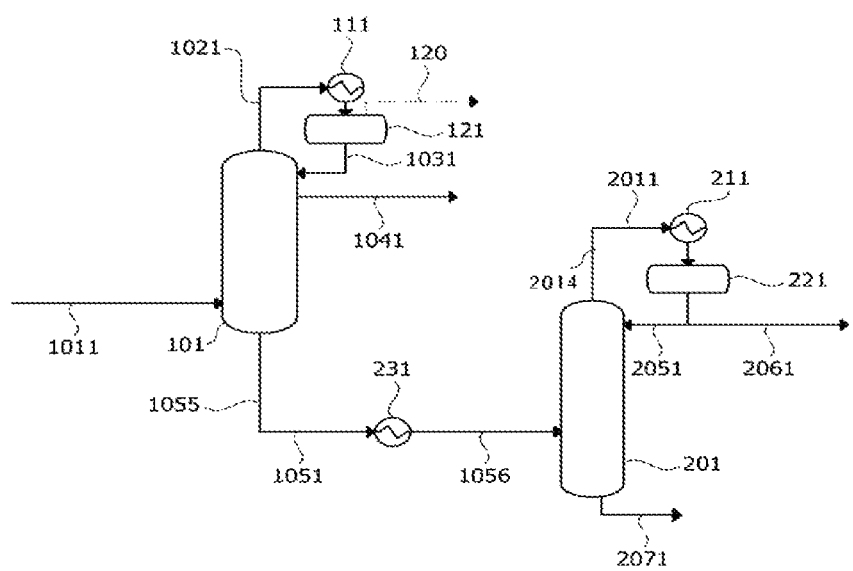

DISTILLATION DEVICE AND DISTILLATION METHOD

CROSS-REFERENCE TO RELATED APPLICATIONS

This application is the national stage of international Application No. PCT/KR2018/006592 filed Jun. 8, 2018, and claims the benefit of priority based on Korean Patent Application No. 10-2017-0071649 filed on Jun. 8, 2017, the disclosures of which are incorporated herein by reference in their entirety.

TECHNICAL FIELD

The present invention relates to a distillation device using two distillation columns, and relates to a distillation device capable of reducing energy consumption by using a vapor recompressor, and a distillation method using the distillation device.

BACKGROUND

Various raw materials such as crude oil are usually a mixture of many chemical substances in many cases, where the mixture is rarely used in the industry as such and usually used after being separated into each compound. A typical chemical process for separating the mixture is a distillation process.

In general, the distillation process evaporates and separates the mixed materials of a binary system or more present in the feedstock by the difference in boiling points. As the distillation device used in this distillation process, a distillation column, a rectification column, a stripping column or a stripping vessel, and the like are used. A low-boiling substance is discharged in the form of overhead vapor from the upper part of the distillation device and a high boiling substance is separated in the form of bottom condensate from the lower part of the distillation device.

In general, the separation of alkanes/alkenes of the same carbon number, such as ethylene/ethane or propylene/propane, requires a high reflux ratio and a large number of theoretical plates because relative volatility is significantly low at a level of 1.04 to 1.5. Thus, in actual processes, there are many cases having a serial connection structure in which two distillation columns are used like one distillation column by connecting the bottom of a first distillation column and the top of a second distillation column to each other.

In order to increase the throughput of such a distillation device, various distillation methods of connecting two distillation columns in parallel can be considered. For example, when the distillation is performed by using the first distillation column as a rectifier and using a structure connected with the second distillation column in parallel, a raw material to be supplied is primarily distilled in the first distillation column and the raw material in which the substance to be separated remains is introduced into the second distillation column and distilled. FIG. 3 is a schematic view showing one example of a distillation device in which two distillation columns are connected in a parallel connection structure. FIG. 3 simulates the configuration of the device in which a raw material (1011) flow to be introduced is distilled in a first distillation column (101), a product effluent flow (1041) is discharged to the upper part of the first distillation column and the bottom flow (1051 or 1055) of the first distillation column is introduced into the second distillation column (201) and distilled, and the product effluent flow (2061) flows out to the upper part of the second distillation column.

When the distillation columns are connected in parallel and operated as in FIG. 3, it is possible to treat the same capacity as that of the case where two distillation columns are operated, but the flow (1051) flowing into the second distillation column must be heated through a heat exchanger (231), and overhead vapor of the second distillation column must be condensed through a condenser (211). In this case, there are problems that energy is consumed in the heat exchanger (231) and the condenser (211), respectively and in particular, when the substance to be separated is a substance having a low boiling point, much energy is consumed for condensation through a refrigerator.

Related Patent Document: Japanese Patent No. 5756900

SUMMARY

The present application relates to a distillation device and a distillation method, and aims to provide a distillation device and a distillation method that energy consumption volume is reduced.

The present application relates to a distillation device. An exemplary distillation device may comprise two distillation columns connected in parallel and a vapor recompressor. By using the distillation device, a high-purity product can be separated and refined, while the consumption of the energy supplied to a re-boiler and/or a condenser is minimized. Hereinafter, the device will be described with reference to drawings, but the drawings are illustrative and the scope of the device is not limited by the drawings.

BRIEF DESCRIPTION OF DRAWINGS

FIG. 1 is a schematic diagram showing one example of the distillation device according to the present application.

FIG. 2 is a schematic diagram showing one example of a distillation device connecting two columns.

FIG. 3 is a schematic diagram showing another example of a distillation device connecting two columns.

DETAILED DESCRIPTION

In this specification, the term 'and/or' is used as a meaning to include at least one of the components listed before and after.

The term such as "first," "second," "one side," and "other side" herein is used to distinguish one component from another component, where each component is not limited by the terms. Hereinafter, in explaining the present application, detailed descriptions of known general functions or configurations are omitted.

The term "line" herein may have substantially the same meaning as a pipe connecting devices, and the term "flow" may mean a movement of a fluid through the line or pipe, and the line, pipe and stream herein may share the same reference numeral.

FIG. 1 is a view illustratively showing a distillation device of the present application.

For example, the distillation device according to the present application comprises a first distillation column (102); a second distillation column (202); a vapor recompressor (242); and a heat exchanger (232). The first distillation column (102) may be equipped with a top condenser (112), wherein a top inlet and a bottom outlet may be formed, an upper inlet and an upper outlet may be formed and a lower inlet may be formed. The second distillation column (202) may be equipped with a top condenser (212), wherein a top inlet and a bottom outlet may be formed, an upper inlet and an upper outlet may be formed and a lower inlet may be formed. The distillation device also may comprise a first supply line (1012) capable of feeding a raw material to the lower inlet of the first distillation column (102); a first connection line (1052) formed so that the flow discharged to the bottom outlet of the first distillation column is introduced into a lower inlet of the second distillation column via the heat exchanger; and second connection lines (2012, 2022, 2032) formed so that the flow discharged to the top outlet of the second distillation column passes through the vapor recompressor and then is introduced into the top condenser of the second distillation column via the heat exchanger. The flow flowing through the first connection line (1052) and the flow flowing through the second connection lines (2012, 2022, 2032) may be formed to be subjected to heat exchange in the heat exchanger (232).

The overhead vapor of the second distillation column (202) introduced into the vapor recompressor (242) is compressed to be subjected to heat exchange with the bottom flow of the first distillation column (102) introduced into the heat exchanger (232) through the first connection line (1052) in the heat exchanger (232), whereby the energy consumed to condense the overhead vapor of the second distillation column (202) in the top condenser (212) of the second distillation column (202) can be reduced.

The specific types of the distillation columns (102, 202) that can be used in the distillation device of the present application are not particularly limited. For example, a distillation column having a general structure can be used, and a plate number and inner diameter of the distillation column, and the like can be appropriately controlled in consideration of purification efficiency and the like. The "heat exchanger" may be a device which is installed separately on the outside of the distillation device and performs heat exchange so that heat transfer smoothly occurs between two fluid flows having different temperatures, the type of which is not particularly limited. In addition, the "condenser" is a device installed separately from the distillation device, which may mean a device for cooling the material flowing out of the distillation device by a method such as bringing it into contact with the cooling water introduced from the outside.

In this specification, the "upper" means a relatively upper portion in the distillation device, and more specifically, when the distillation device is bisected perpendicularly to the longitudinal direction, for example, the length or height direction of the distillation device, it may mean the upper part of the divided two areas. In addition, the "lower" means a relatively lower portion in the distillation device, and more specifically, when the distillation device is bisected perpendicularly to the longitudinal direction, for example, the length or height direction of the distillation device, it may mean the lower part of the divided two areas. Furthermore, the "top" of the distillation device means the uppermost portion of the distillation device, which may be located at the upper part of the distillation device as described above, and the "bottom" of the distillation device means the lowermost portion of the distillation device, which may be located at the lower part of one distillation device as described above. In one example, an intermediate part region may be present between the upper part and the lower part of the distillation device, where the upper, intermediate and lower regions of the distillation device may be used herein as relative concepts to each other. For example, when the distillation device has been bisected in the longitudinal direction, the distillation device can be divided into upper and lower regions, in which case distillation can occur in the upper and lower regions. When the distillation device has been trisected in the longitudinal direction, the distillation device can be divided into upper, intermediate and lower regions, in which case distillation can occur in all the upper, intermediate and lower regions.

The vapor recompressor (242) may be a device capable of compressing vapor using external power, may be a device for increasing the temperature by compressing vapor, and may be a device for using latent heat and/or sensible heat of the compressed vapor which raises the temperature with the vapor recompressor (242) as a heat source of a process such as evaporation or distillation and drying. The distillation device of the present application compresses the overhead vapor of the second distillation column (202) with the vapor recompressor (242) and the compressed overhead vapor of the second distillation column (202) is subjected to heat exchange with the flow flowing out of the bottom of the first distillation column (102) and introduced into the second distillation column (202), whereby the energy consumed to condense the overhead vapor of the second distillation column (202) in the top condenser (212) of the second distillation column (202) can be reduced.

The distillation device according to the present application can be applied by a vapor recompressor having various types and operating principles. The vapor recompressor is not particularly limited, but may be, for example, a mechanical vapor recompressor (MVR), where a reciprocating compressor, a screw compressor, a rotary compressor, a centrifugal compressor, or the like may be used, without being limited thereto.

In one example of the present application, the lower inlet of the first distillation column may be located at the lowermost stage of the theoretical plate number calculated on the basis of the top. The lower inlet of the first distillation column may be 80% or more, 85% or more, or 90% or more of the theoretical plate number calculated on the basis of the top, for example, may be 95% or more, and may be, for example, 100% or less. In this specification, the "theoretical plate number" may mean the number of imaginary regions or stages in which two phases such as vapor phase and liquid phase in the distillation column are in equilibrium with each other. The fact that the lower inlet is located at 80% of the theoretical plate number calculated on the basis of the top may mean that it is located at Stage 80, for example, assuming that the top is Stage 1 in a distillation column having a theoretical plate number of 100 stages. Furthermore, the fact that the lower inlet is located at 100% of the theoretical plate number calculated on the basis of the top may mean, for example, that the lower inlet is located at the bottom of the distillation column.

The first distillation column of the distillation device according to the present application may have a shape such that the rectifying section is longer than the stripping section by placing the lower inlet in the above range, thereby improving the purity of the low-boiling substance flowing out to the upper part of the first distillation column. Furthermore, in one example, the location of the lower inlet of the first distillation column satisfies the above range, so that the first distillation column can function substantially as a rectifying column.

In one example of the present application, the lower inlet of the second distillation column may be located at 60% to 90% of the theoretical plate number calculated on the basis of the top. The location of the lower inlet of the second distillation column may be 60% or more, 65% or more, 70% or more, or 75% or more of the theoretical plate number calculated on the basis of the top, for example, may be 80% or more, may be 90% or less, 89% or less, 88% or less, or 87% or less, and may be, for example, 85% or less. The second distillation column of the distillation device according to the present application may also have a shape such that the rectifying section is longer than the stripping section by placing the lower inlet in the above range, thereby improving the purity of the low-boiling substance flowing out to the upper part of the second distillation column. Furthermore, in one example, the location of the lower inlet of the second distillation column satisfies the above range, so that the second distillation column can function substantially as a rectifying column.

In one example, the distillation device according to the present application may be a device for separating basic fractions produced in a naphtha cracking process. In the naphtha cracking process, naphtha produced in a petroleum refining process is pyrolyzed in the NCC (naphtha cracking center) to produce C2, C3 and C4 fractions and BTX, and the like, where the distillation device according to the present application can be used for separating and purifying them.

In one example of the present application, the product flowing out of the upper outlet of the first distillation column and the upper outlet of the second distillation column in the distillation device may be an alcohol having 1 to 12 carbon atoms, 1 to 10 carbon atoms, 2 to 8 carbon atoms, 2 to 6 carbon atoms or 2 to 4 carbon atoms, and may be, for example, ethylene. By distilling ethylene using the distillation device according to the present application, high-purity ethylene can be purified using two distillation columns and the load of the refrigeration system used in the top condenser of the second distillation column can be reduced.

In one example, the absolute value ($|T_2-T_1|$) of the difference between the temperature ($T_2$) of the overhead vapor flow (2013) passing through the second connection line (2012) connecting the top outlet of the second distillation column (202) to the vapor recompressor (242)) in the distillation device of the present application and the temperature ($T_1$) of the bottom discharge flow (1053) of the first distillation column (102) discharged to the bottom outlet of the first distillation column (102) to pass through the heat exchanger (232) through the first connection line (1052) and then flowing into the second distillation column (202) may be 40° C. or lower. The absolute value ($|T_2-T_1|$) of the temperature difference may be 36° C. or lower, 32° C. or lower, 28° C. or lower, 24° C. or lower, 20° C. or lower, or 16° C. or lower, but is not limited thereto, and the lower limit is not particularly limited, but may be, for example, 1° C. or higher, 3° C. or higher, 5° C. or higher, or 7° C. or higher. The absolute value ($|T_2-T_1|$) of the difference between the temperature ($T_2$) of the overhead vapor flow passing through the second connection line connecting the top outlet of the second distillation column to the vapor recompressor and the temperature ($T_1$) of the bottom discharge flow of the first distillation column discharged to the bottom outlet of the first distillation column to pass through the heat exchanger through the first connection line and then flowing into the second distillation column satisfies the above range, whereby excellent heat exchange efficiency can be shown even with a small amount of energy supply using the vapor recompressor and the energy supplied to heat the bottom flow of the first distillation column flowing into the second distillation column and/or the energy supplied to the top condenser of the second distillation column can be reduced.

In one example according to the present application, the absolute value ($|T_3-T_4|$) of the difference between the temperature ($T_3$) of the bottom flow (1054) of the first distillation column (102) discharged to the bottom outlet of the first distillation column (102) and the temperature ($T_4$) of the bottom discharge flow (1053) of the first distillation column (102) discharged to the bottom outlet of the first distillation column (102) to pass through the heat exchanger (232) through the first connection line (1052) and then flowing into the second distillation column (202) may be 5° C. or lower. The absolute value of the temperature difference may be, for example, 4° C. or lower, 3° C. or lower, or 2° C. or lower and may be 0° C. or higher, but is not limited thereto. When the temperature difference between before and after the bottom flow of the first distillation column passes through the heat exchanger satisfies the above range, the heat exchange is performed using latent heat, whereby the energy efficiency can be increased and the energy supplied to the top condenser of the second distillation column can be reduced.

The temperatures $T_1$ and $T_4$ represent temperatures for the bottom discharge flow (1053) of the first distillation column (102) at the same point which is discharged to the bottom outlet of the first distillation column (102) to pass through the heat exchanger (232) through the first connection line (1052) and then flows into the second distillation column (202).

The present application also relates to a distillation method, where the distillation method can be performed by the above-described distillation device. An exemplary distillation method comprises steps of: introducing a feedstock into a first distillation column to distill it; and introducing the bottom flow of the first distillation column into a second distillation column to distill it, where the top flow of the second distillation column may be introduced into a vapor recompressor and compressed, and the bottom flow of the first distillation column may be heat exchanged with the compressed top flow of the second distillation column and introduced into the second distillation column. In the distillation method of the present application, the detailed description of the distillation device is the same as that described in the above-mentioned distillation device, which will be omitted.

In one example according to the distillation method of the present application, the absolute value ($|T_2-T_1|$) of the difference between the temperature ($T_2$) of the overhead vapor flow (2013) passing through the second connection line (2012) connecting the top outlet of the second distillation column (202) to the vapor recompressor (242)) and the temperature ($T_1$) of the bottom discharge flow (1053) of the first distillation column (102) discharged to the bottom outlet of the first distillation column (102) to pass through the heat exchanger (232) through the first connection line (1052) and then flowing into the second distillation column (202) may be 40° C. or lower. The absolute value ($|T_2-T_1|$) of the temperature difference may be 36° C. or lower, 32° C. or lower, 28° C. or lower, 24° C. or lower, 20° C. or lower, or 16° C. or lower, but is not limited thereto, and the lower limit is not particularly limited, but may be, for example, 1° C. or higher, 3° C. or higher, 5° C. or higher, or 7° C. or higher. The absolute value ($|T_2-T_1|$) of the difference between the temperature ($T_2$) of the top flow of the second distillation column and the temperature ($T_1$) of the bottom flow of the first distillation column discharged from the heat exchanger to flow into the second distillation column satisfies the above range, whereby excellent heat exchange efficiency can be shown even with a small amount of energy supply using the vapor recompressor and the energy supplied to heat the bottom flow of the first distillation column flowing into the second distillation column and/or the energy supplied to the top condenser of the second distillation column can be reduced.

In one example according to the present application, the temperature ($T_2$) of the top flow of the second distillation column and the temperature ($T_1$) of the bottom flow of the first distillation column discharged from the heat exchanger to flow into the second distillation column are not particularly limited, as long as the absolute value ($|T_2-T_1|$) of the difference between the temperature ($T_2$) of the top flow of the second distillation column and the temperature ($T_1$) of the bottom flow of the first distillation column discharged from the heat exchanger to flow into the second distillation column satisfies the above range. The temperature ($T_2$) of the top flow of the second distillation column and the temperature ($T_1$) of the bottom flow of the first distillation column discharged from the heat exchanger to flow into the second distillation column may vary depending on the target material to be separated and the separation conditions, and the like, and for example, if the product flowing out of the upper outlet of the first distillation column and the upper outlet of the second distillation column is ethylene, the temperature of the bottom flow flowing out of the bottom outlet of the first distillation column may be from −15° C. to −30° C., and the temperature of the top flow of the second distillation column may be from −20° C. to −35° C., but is not limited thereto.

In one example according to the distillation method of the present application, the absolute value ($|T_3-T_4|$) of the difference between the temperature ($T_3$) of the bottom flow (1054) of the first distillation column (102) discharged to the bottom outlet of the first distillation column (102) and the temperature ($T_4$) of the bottom discharge flow (1053) of the first distillation column (102) discharged to the bottom outlet of the first distillation column (102) to pass through the heat exchanger (232) through the first connection line (1052) and then flowing into the second distillation column (202) may be 5° C. or lower. The absolute value of the temperature difference may be, for example, 4° C. or lower, 3° C. or lower, or 2° C. or lower and may be 0° C. or higher, but is not limited thereto. When the temperature difference between before and after the bottom flow of the first distillation column passes through the heat exchanger satisfies the above range, the bottom flow of the first distillation column discharged to the bottom outlet of the first distillation column may be vaporized in the procedure of passing through the heat exchanger. In this specification, the fact to be "vaporized" may mean that the material changes from a liquid phase to a gas phase, and for example, it may mean that the liquid becomes the gas. The heat exchange is performed using latent heat of the bottom flow of the first distillation column, whereby the energy efficiency can be increased and the energy supplied to the top condenser of the second distillation column can be reduced.

The temperature of the bottom flow discharged to the bottom outlet of the first distillation column and the temperature of the bottom flow of the first distillation column flowing into the second distillation column after heat exchange with the compressed top flow of the second distillation column and/or the temperature of the top flow of the second distillation column discharged to the top outlet of the second distillation column being controlled within the above-discussed ranges, the product can be discharged to the upper outlets of the first distillation column and the second distillation column with high purity, improve the heat exchange efficiency through the vapor recompressor to reduce the energy consumption volume of various processes that require a refrigeration system for condensation, and in particular, greatly reduce the energy consumption volume of the alkane/alkene separation process.

In one example, the distillation method according to the present application can discharge low-boiling substances from the upper part of the first distillation column and the upper part of the second distillation column, and discharge high-boiling substances from the bottom of the second distillation column. In this specification, the "high-boiling substance" may mean a substance having a relatively high boiling point relative to other substances in a mixture, and the "low-boiling substance" may mean a substance having a relatively low boiling point relative to other substances in a mixture. The high-boiling substance may mean a substance having a boiling point of −120° C. or higher or −110° C. or higher at room temperature (25° C.) and normal pressure (1 atm), and the upper limit is not particularly limited. The low-boiling substance may have a boiling point of 200° C. or lower at room temperature (25° C.) and normal pressure (1 atm), and the lower limit is not particularly limited. The boiling point may mean a boiling point of a substance, which may be the same or different depending on the kind of the substance and may vary depending on the temperature and/or the pressure. The high-boiling substance and the low-boiling substance can be divided by the difference in the relative boiling points. In this specification, the high-boiling substance may be a substance having a high boiling point relative to the low-boiling substance at a temperature and a pressure for separating the mixture, and the low-boiling substance may mean a substance having a low boiling point relative to the high-boiling substance at a temperature and a pressure for separating the mixture.

In one example, the distillation method according to the present application can control so that the purity of the low-boiling substance is 99 wt % or more, and the purity of the high-boiling substance is 99 wt % or more. By using the above-described distillation device, the distillation method of the present application can control so that the low-boiling substance discharged from the upper part of the first distillation column and/or the second distillation column satisfies the above purity and control so that the high-boiling substance satisfies the above purity.

In one example of the application, the low-boiling substance may be an alkene and the high-boiling substance may be an alkane, and for example, the alkene and/or the alkane may be an alkene and/or an alkane, having 1 to 12 carbon atoms, 1 to 10 carbon atoms, 2 to 8 carbon atoms, 2 to 6 carbon atoms or 2 to 4 carbon atoms. The alkene and/or the alkane may be, for example, a product of a naphtha cracking process, which may discharge ethane as a high-boiling substance and ethylene as a low-boiling substance, or may discharge propane as a high-boiling substance and propylene as a low-boiling substance, but is not limited thereto.

According to the distillation device of the present application, the energy supplied for heating the bottom flow of the first distillation column flowing into the second distillation column can be reduced by compressing the overhead vapor of the second distillation column with the vapor recompressor to flow into the heat exchanger and heating the bottom flow of the first distillation column. In addition, the energy consumption volume of the condenser supplied to condense the overhead vapor of the second distillation column is reduced, whereby the energy used in the entire process can be reduced.

Hereinafter, the present application will be described in detail through the example according to the present application, but the scope of the present application is not limited by the following example.

EXAMPLE

Among C2 components produced in a naphtha cracking process, ethylene and ethane were separated using the distillation device illustrated in FIG. 1. As illustrated in FIG. 1, the first feedstock supply line (1012) was connected to the lower inlet of the first distillation column (102), and the bottom outlet of the first distillation column (102) was connected to the heat exchanger (232) and the lower inlet of the second distillation column (202) through the first connection line (1052), and the lower inlet of the second distillation column (202). The top outlet of the second distillation column (202) was connected to the vapor recompressor (242), the heat exchanger (232), the valve (252) and the top condenser (212) of the second distillation column (202) through the second connection lines (2012, 2022, 2032). The heat exchanger (232) was installed so that the first connection line (1052) could be subjected to heat exchange with the second connection lines (2012, 2022, 2032).

The feedstock was introduced into the lower inlet of the first distillation column (102) at a rate of 198,846 kg/hr through the first feedstock supply line (1012) and distilled, and the flow discharged to the bottom outlet of the first distillation column (102) was introduced into the bottom inlet of the second distillation column (202) through the first connection line (1052) and distilled.

The overhead vapor of the first distillation column (102) introduced into the top condenser (112) of the first distillation column (102) via the top discharge line (1022) of the first distillation column (102) was condensed and introduced into the storage tank (122) to be stored, and then it was refluxed to the first distillation column (102) through the upper inflow line (1032) of the first distillation column (102) or discharged as a product through the product discharge line (1030).

The overhead vapor of the second distillation column (202) was introduced into the top condenser (212) of the second distillation column (202) through the second connection lines (2012, 2022, 2032), which was condensed and introduced into the storage tank (222) to be stored, and then it was refluxed to the second distillation column (202) through the upper inflow line (2052) of the second distillation column (202). Ethylene as the low-boiling substance was separated into the upper discharge line (1042) of the first distillation column (102) and the upper discharge line (2062) of the second distillation column (202) and ethane as the high-boiling substance was separated from the bottom discharge line (2072) of the second distillation column (202).

The overhead vapor of the second distillation column (202) was introduced into the vapor recompressor (242) via the second connection line (2012) and compressed, and then it was introduced into the heat exchanger (232) through the second connection line (2022). The bottom discharge flow of the first distillation column (102) flowing through the first connection line (1052) was subjected to heat exchange with the overhead vapor of the second distillation column (202) flowing through the second connection lines (2012, 2022) through the heat exchanger (232), and then introduced into the lower inlet of the second distillation column (202). The flow discharged through the bottom outlet of the first distillation column (102) to flow into the lower inlet of the second distillation column (202) was maintained at 153,244 kg/hr, the energy supply quantity through a bottom reboiler (not shown) of the second distillation column (202) was 11.36 Gcal/hr and the energy supplied to the vapor recompressor (242) was 1,367 KW. The reflux ratio of the first distillation column (102) was controlled to be 4.18 and the reflux ratio of the second distillation column (202) was controlled to be 3.06. In addition, in the top flow of the first distillation column (102), the temperature was −36.24° C. and the pressure was maintained at 15.54 kg/cm$^2$, and in the overhead vapor flow (2013) passing through the second connection line (2012) through the top outlet of the second distillation column (202) was connected to the vapor recompressor (242), the temperature ($T_2$) was −36.24° C. and the pressure was maintained at 15.54 kg/cm$^2$. The temperature ($T_3$) of the bottom flow (1054) of the first distillation column (102) discharged to the bottom outlet of the first distillation column (102) was maintained at −24.00° C. and the temperatures ($T_1$, $T_4$) of the bottom discharge flow (1053) of the first distillation column (102) discharged to the bottom outlet of the first distillation column (102) to pass through the heat exchanger (232) through the first connection line (1052) and then flowing into the second distillation column (202) were 20.12° C.

Comparative Example 1

As illustrated in FIG. 2, among C2 components produced in a naphtha cracking process, ethylene and ethane were separated by connecting the first distillation column (101) and the second distillation column (201) in series. The feedstock was introduced into the feedstock inlet of the second distillation column (201) through the second feedstock supply line (21) and distilled, the overhead vapor of the second distillation column (201) was introduced into the first distillation column (101) through the top discharge line (241) of the second distillation column (201) and distilled, and the overhead vapor of the first distillation column (101) introduced into the top condenser (91) of the first distillation column (101) via the top discharge line (81) of the first distillation column (101) was condensed and introduced into the storage tank (131) to be stored, and then it was refluxed to the first distillation column (101) through the upper discharge line (110) of the first distillation column (101) or discharged as a product through the product discharge line (130).

The overhead vapor of the second distillation column (201) introduced into the first distillation column (101) was distilled, the bottom condensate of the first distillation column (101) was introduced into the second distillation column (201) through the bottom discharge line (151) of the first distillation column (101), and the bottom condensate discharged to the bottom discharge line (251) of the second distillation column (201) was heated through the bottom reboiler (261) of the second distillation column (201) and refluxed to the second distillation column (201) through the lower inflow line (210) of the second distillation column (201).

Ethylene as the low-boiling substance was separated into the upper discharge line (141) of the first distillation column (101) and ethane as the high-boiling substance was separated from the bottom discharge line (271) of the second distillation column (201). The top temperature of the first distillation column (101) was −36.24° C., the pressure was maintained at 15.54 kg/cm$^2$, the energy supply quantity through the bottom reboiler (261) of the second distillation column (101) was 18.89 Gcal/hr, and the reflux ratio was controlled to 5.33.

Comparative Example 2

Among C2 components produced in a naphtha cracking process, ethylene and ethane were separated using the distillation device illustrated in FIG. 3. As illustrated in FIG. 3, the first feedstock supply line (1011) was connected to the lower inlet of the first distillation column (101) and the bottom outlet of the first distillation column (101) was connected to the heat exchanger (231) and the lower inlet of the second distillation column (201) through the first connection line (1051).

The feedstock was introduced into the lower inlet of the first distillation column (101) at a rate of 198,846 kg/hr through the first feedstock supply line (1011) and distilled, and the flow discharged to the bottom outlet of the first distillation column (101) was introduced into the lower inlet of the second distillation column (201) through the first connection line (1051) and distilled.

The overhead vapor of the first distillation column (101) introduced into the top condenser (111) of the first distillation column (101) via the top discharge line (1021) of the first distillation column (101) was condensed and introduced into the storage tank (121) to be stored, and then it was refluxed to the first distillation column (101) through the upper inflow line (1031) of the first distillation column (101) or discharged as a product through the product discharge line (120).

The overhead vapor of the second distillation column (201) introduced into the top condenser (211) of the second distillation column (201) via the top discharge line (2011) of the second distillation column (201) was condensed and introduced into the storage tank (221) to be stored, and then refluxed to the second distillation column (201) through the upper inflow line (2051) of the second distillation column (201). Ethylene as the low-boiling substance was separated into the upper discharge line (1041) of the first distillation column (101) and the upper discharge line (2061) of the second distillation column (202), and ethane as the high-boiling substance was separated from the bottom discharge line (2071) of the second distillation column (201).

The bottom discharge flow of the first distillation column (101) flowing through the first connection line (1051) was introduced into the heat exchanger (231) to be subjected to heat exchange and then introduced into the lower inlet of the second distillation column (201). The flow discharged through the bottom outlet of the first distillation column (101) to flow into the lower inlet of the second distillation column (201) was maintained at a rate of 153,244 kg/hr and the energy supply quantity through the bottom reboiler of the second distillation column (201) was 11.35 Gcal/hr. The reflux ratio of the first distillation column (101) was 4.18 and the reflux ratio of the second distillation column (201) was controlled to be 3.06. The temperature of the top flow of the first distillation column (101) was −36.24° C., the pressure was maintained at 15.54 kg/cm², and the temperature ($T_2$) of the overhead vapor flow (2014) discharged to the top outlet of the second distillation column (201) was −36.24° C., and the pressure was maintained at 15.54 kg/cm². The temperature ($T_3$) of the bottom flow (1055) of the first distillation column (101) discharged to the bottom outlet of the first distillation column (101) was maintained at −24.00° C. and the temperatures ($T_1$, $T_4$) of the bottom discharge flow (1056) discharged to the bottom outlet of the first distillation column (101) to pass through the heat exchanger (231) through the first connection line (1051) and then flowing into the second distillation column (201) were 9.01° C.

TABLE 1

|  |  | Comparative Example | | Example |
|---|---|---|---|---|
|  |  | 1 | 2 |  |
| Feed Rate (kg/hr) | First Distillation Column |  | 198,846 | 198,846 |
|  | Second Distillation Column | 198,689 | 153,244 | 153,244 |
| Ethylene Product (kg/hr) | First Distillation Column | 150,015 | 45,162 | 45,162 |
|  | Second Distillation Column | — | 104,899 | 104,899 |
| Liquid Mass Flow Rate in Column (kg/hr) | First Distillation Column | 444,632 | 153,606 | 153,606 |
|  | Second Distillation Column | 444,632 | 353,760 | 353,760 |
| Condensor Duty (Gcal/hr) | First Distillation Column | −49.13 | −16.19 | −16.19 |
|  | Second Distillation Column |  | −37.87 | −26.38 |
|  | Total | −49.13 | −54.06 | −42.57 |
| Reboiler Duty (Gcal/hr) | First Distillation Column | — | — |  |
|  | Second Distillation Column | 18.89 | 11.35 | 11.36 |
|  | Total | 18.89 | 11.35 | 11.36 |
| ΔShaftwork (KW) |  | — | — | 1,267 |

In the case of separating ethylene and ethane using the distillation devices of Example and Comparative Examples, the feed rate of the feedstock, the product amount of ethylene, the mass flow rate of the liquid in the column, the energy supplied to the condenser, the energy supplied to the reboiler and the energy supplied to the vapor recompressor were shown in Table 1. In the case of Comparative Example 2 and Example, the feed rate means the amount of the flow discharged from the bottom of the first distillation column to flow into the second distillation column, and the mass flow rate of the liquid in the column means the mass flow rate of the liquid going down to the lower stage for each tray from each distillation column and the shaftwork means the amount of the energy supplied to the vapor recompressor. Referring to Table 1, when ethylene and ethane are separated using the distillation device according to the example of the present application, more products can be produced using the same sized distillation column, as compared with Comparative Example 1, and even when only 1,267 KW is supplied to the vapor recompressor, the energy consumption volume required for the top condenser of the second distillation column can be greatly reduced, as compared with Comparative Examples 1 and 2.

EXPLANATION OF REFERENCE NUMERALS 101, 102: first distillation column
201, 202: second distillation column
91, 111, 112: top condenser of the first distillation column
211, 212: top condenser of the second distillation column
121, 122, 131, 221, 222: storage tank
231, 232: heat exchanger
242: vapor recompressor
252: valve
1011, 1012: first feedstock supply line
21: second feedstock supply line
151: bottom discharge line of the first distillation column
241, 2011: top discharge line of the second distillation column
210: lower inflow line of the second distillation column
261: bottom reboiler of the second distillation column
81, 1021, 1022: top discharge line of the first distillation column
141, 1041, 1042: upper discharge line of the first distillation column
1051, 1052: first connection line
2012, 2022, 2032: second connection line
2061, 2062: upper discharge line of the second distillation column
120, 130, 1030: product discharge line
110, 1031, 1032: upper inflow line of the first distillation column
2051, 2052: upper inflow line of the second distillation column
251, 271, 2071, 2072: bottom discharge line of the second distillation column
1054, 1055: bottom flow of the first distillation column discharged to the bottom outlet of the first distillation column
1053, 1056: bottom discharge flow of the first distillation column discharged to the bottom outlet of the first distillation column to pass through the heat exchanger through the first connection line, and then flowing into the second distillation column
2013, 2014: overhead vapor flow discharged from the top outlet of the second distillation column

The invention claimed is:
1. A distillation device comprising:
a first distillation column having a first top outlet, a first bottom outlet, a first upper inlet, a first upper outlet and a first lower inlet, wherein the first upper inlet, the first upper outlet and the first lower inlet are located between the first top outlet and the first bottom outlet, and wherein the first lower inlet is located below the first upper inlet and the first upper outlet;
a second distillation column equipped with a top condenser and a bottom reboiler, and having a second top outlet, a second bottom outlet, a second upper inlet, a second upper outlet and a second lower inlet, wherein the second upper inlet, the second upper outlet and the second lower inlet are located between the second top outlet and the second bottom outlet, and wherein the second lower inlet is located below the second upper inlet and the second upper outlet;
a vapor recompressor;
a heat exchanger;
a first supply line supplying a feedstock to the lower inlet of the first distillation column;
a first connection line transferring a first bottom flow discharged from the first bottom outlet of the first distillation column to the second lower inlet of the second distillation column via the heat exchanger;
a second connection line transferring a second top flow discharged from the second top outlet of the second distillation column to the top condenser of the second distillation column via the heat exchanger after passing through the vapor recompressor,
wherein the first bottom flow flowing through the first connection line and the second top flow flowing through the second connection line after passing through the vapor recompressor are heat-exchanged in the heat exchanger prior to the first connection line transferring the first bottom flow discharged from the first bottom outlet of the first distillation column to the second lower inlet of the second distillation column via the heat exchanger.

2. The distillation device according to claim 1, wherein the vapor recompressor is a mechanical vapor recompressor (MVR).

3. The distillation device according to claim 1, wherein the first lower inlet of the first distillation column is located at 80% to 100% of the theoretical plate number calculated from the top of the first distillation column.

4. The distillation device according to claim 1, wherein the second lower inlet of the second distillation column is located at 60% to 90% of the theoretical plate number calculated from the top of the second distillation column.

5. The distillation device according to claim 1, wherein the product discharged from the first upper outlet of the first distillation column and the second upper outlet of the second distillation column is an alkene having 2 to 12 carbon atoms.

6. The distillation device according to claim 1, wherein an absolute value ($|T_2-T_1|$) of the difference between a temperature ($T_2$) of the second top flow discharged from the second distillation column and a temperature ($T_1$) of the first bottom flow discharged from the first distillation column after passing through the heat exchanger and then flowing into the second distillation column is 40° C. or lower.

7. The distillation device according to claim 1, wherein an absolute value ($|T_3-T_4|$) of the difference between a temperature ($T_3$) of a first bottom flow discharged from the first distillation column and a temperature ($T_4$) of the first bottom flow discharged from the first distillation column after passing through the heat exchanger and then flowing into the second distillation column is 5° C. or lower.

8. A distillation method of a feedstock using the distillation device of claim 1, comprising steps of: introducing the feedstock into the first distillation column; and introducing the first bottom flow discharged from the first distillation column to the second distillation column,
wherein the second top flow discharged from the second distillation column is introduced into the vapor recompressor and compressed, and the first bottom flow of the first distillation column is heat-exchanged with the compressed second top flow of the second distillation column and then introduced into the second distillation column.

9. The distillation method according to claim 8, wherein an absolute value ($|T_2-T_1|$) of the difference between a temperature ($T_2$) of the second top flow discharged from the second distillation column and a temperature ($T_1$) of the first bottom flow discharged from the first distillation column after passing through the heat exchanger and then flowing into the second distillation column is 40° C. or lower.

10. The distillation method according to claim 8, wherein an absolute value ($|T_3-T_4|$) of the difference between a temperature ($T_3$) of the first bottom flow discharged from the first distillation column and a temperature ($T_4$) of the first bottom flow discharged from the first distillation column after passing through the heat exchanger and then flowing into the second distillation column is 5° C. or lower.

11. The distillation method according to claim 10, wherein the first bottom flow is vaporized in the process of passing through the heat exchanger.

12. The distillation method according to claim 8, wherein a low-boiling substance is discharged from the first upper outlet of the first distillation column and the second upper outlet of the second distillation column, and a high-boiling substance is discharged from the second bottom outlet of the second distillation column.

13. The distillation method according to claim 12, wherein the purity of each of the low-boiling substance and the high-boiling substance is 99 wt % or more.

14. The distillation method according to claim 12, wherein the low-boiling substance is an alkene having 1 to 12 carbon atoms.

15. The distillation method according to claim 12, wherein the high-boiling substance is an alkane having 1 to 12 carbon atoms.

* * * * *